United States Patent [19]
Merkatoris et al.

[11] Patent Number: 5,296,080
[45] Date of Patent: Mar. 22, 1994

[54] APPARATUS FOR APPLYING AN ELASTIC WAISTBAND TO A DISPOSABLE DIAPER

[75] Inventors: John Merkatoris; James Hertel, both of Green Bay, Wis.

[73] Assignee: Paper Converting Machine Company, Green Bay, Wis.

[21] Appl. No.: 183,060

[22] Filed: Apr. 19, 1988

[51] Int. Cl.⁵ .............................................. B32B 31/00
[52] U.S. Cl. .................... 156/496; 156/519; 156/552; 156/568; 156/164; 156/229; 221/217
[58] Field of Search ............... 156/161, 163, 164, 177, 156/179, 229, 265, 303, 434, 439, 494, 495, 519, 552, 568, 496; 28/102; 26/88, 90, 77, 99; 604/383, 385.2; 221/214, 217; 271/18.3

[56] References Cited

U.S. PATENT DOCUMENTS

| | | | |
|---|---|---|---|
| 30,801 | 12/1860 | Cleveland | 26/90 |
| 485,400 | 11/1892 | Watson | 26/90 X |
| 1,014,916 | 1/1912 | Stevens | 156/439 |
| 2,483,339 | 9/1949 | Gardner et al. | 26/87 |
| 2,702,406 | 2/1955 | Reed | 26/88 X |
| 3,179,348 | 4/1965 | Nystrand et al. | 242/56 R |
| 3,444,020 | 5/1969 | Kalwaites | 156/177 X |
| 3,639,917 | 2/1972 | Althouse | 2/270 |
| 3,805,341 | 4/1974 | Jense | 156/439 X |
| 4,284,454 | 8/1981 | Joa | 156/229 X |
| 4,349,185 | 9/1982 | Small et al. | 270/32 |
| 4,364,787 | 12/1982 | Radzins | 156/164 |
| 4,494,740 | 1/1985 | Noboru et al. | 26/90 X |
| 4,523,969 | 6/1985 | Spencer | 156/161 |
| 4,573,991 | 3/1986 | Pieniak et al. | 604/385.2 |
| 4,608,115 | 8/1986 | Schroth et al. | 156/164 X |
| 4,642,150 | 2/1987 | Stemmler | 156/164 |
| 4,726,874 | 2/1988 | VanVliet | 156/495 |
| 4,735,673 | 4/1988 | Piron | 156/496 |

FOREIGN PATENT DOCUMENTS

| | | |
|---|---|---|
| 0139620 | 5/1985 | European Pat. Off. . |
| 0159627 | 10/1985 | European Pat. Off. . |
| 0236032 | 9/1987 | European Pat. Off. . |
| 2492310 | 4/1982 | France . |

Primary Examiner—David A. Simmons
Assistant Examiner—Chester T. Barry
Attorney, Agent, or Firm—Tilton, Fallon, Lungmus & Chestnut

[57] ABSTRACT

A method and apparatus for applying an elastic waistband to disposable diapers utilizing canted pin-equipped wheels where an elastic patch is applied to the wheels when the wheel peripheries are close together and then stripping the patches from the pins and applying them to a diaper component web when the wheels are further apart.

1 Claim, 1 Drawing Sheet

APPARATUS FOR APPLYING AN ELASTIC WAISTBAND TO A DISPOSABLE DIAPER

BACKGROUND AND SUMMARY OF INVENTION:

This invention relates to a method and apparatus for applying an elastic waistband to a disposable diaper and, more particularly, to a unique method and apparatus for stretching the waistband in manufacture so as to develop the necessary gathering in the final product.

Illustrative of the prior art for making a diaper product with an elastic waistband is co-owned U.S. Pat. No. 4,523,969. This embodied complicated grippers to provide the stretching of the elastic material. In contrast to that, the instant invention provides a very simple method and apparatus for stretching the elastic material for application to one of the continuous diaper component webs—usually the non-woven web. Disposable diapers historically have included the moisture-pervious (non-woven) for positioning adjacent the body of the infant, an absorbent batt, and an outer web of moisture-impervious material, normally polyethylene.

According to the instant invention, a pair of canted wheels equipped with generally radially extending pins on the peripheries are employed to receive the elastic material at a first position and to deposit the stretched material onto one of the webs at a second position wherein the wheel peripheries are farther apart than at the first position. Thus, rotation of the wheels automatically stretches the web in a simple, uncomplicated manner and which is adapted for high speed, rotary operation.

Pins for mounting webs in converting are well known as seen in co-owned Patent 3,179,348. However, there is no showing that the pins move relative to each other for stretching a web therebetween.

Other advantages and objects of the invention may be seen in the details of the ensuing specification. The invention is explained in conjunction with the accompanying drawing, in which --

DETAILED DESCRIPTION

Figure 1:
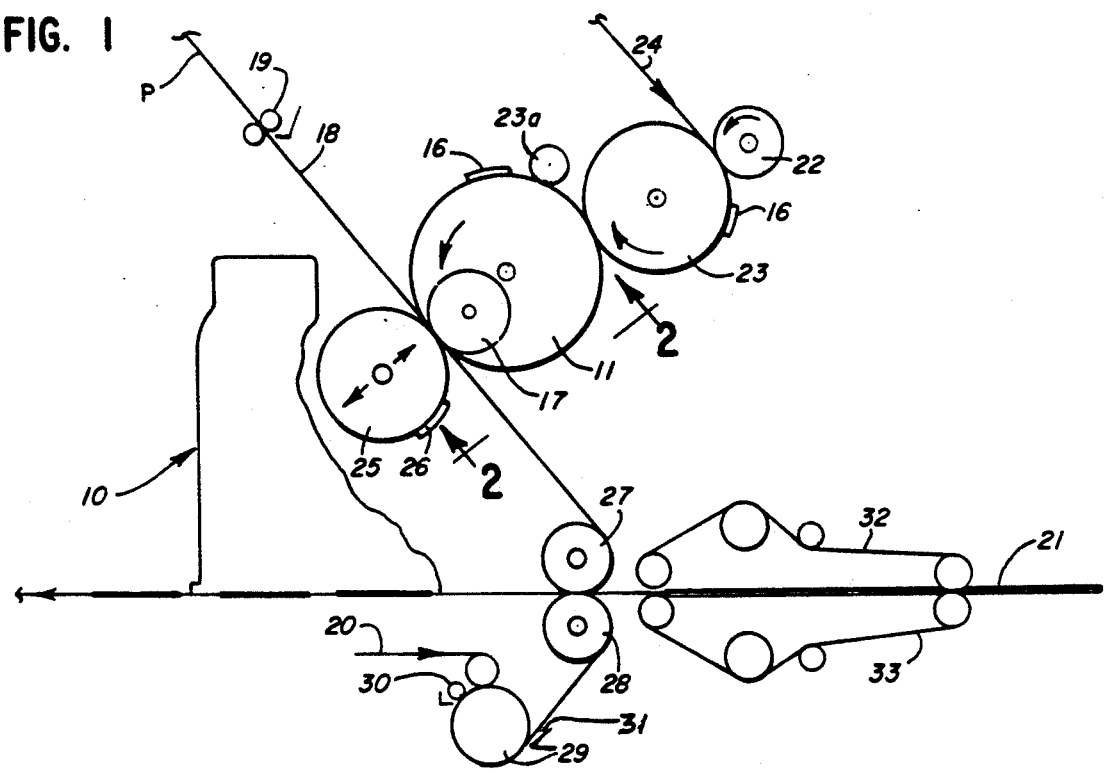
FIG. 1 is a side elevational view (essentially schematic) of the apparatus employed in the practice of the invention.

Referring first to FIG. 1, the numeral 10 generally designates the frame of the machine which is shown only fragmentarily. Normally in the art of paper converting, a pair of side frames are employed (united by suitable cross members) to define the path of operation. Thus, one of the side frames is seen in FIG. 2 and designated 10a.

Figure 2:
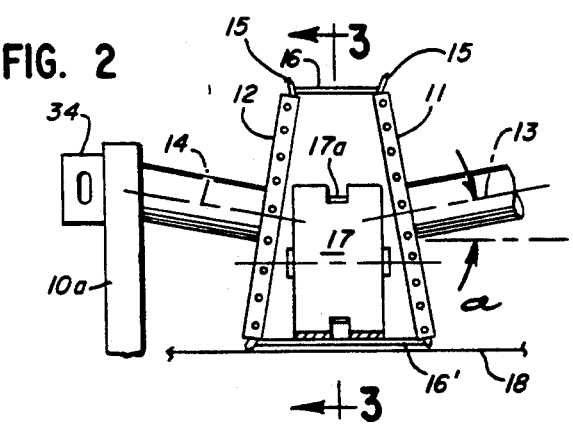
FIG. 2 is a fragmentary end elevational view such as would be seen along the sight line 2—2 applied to FIG. 1.
Figure 3:
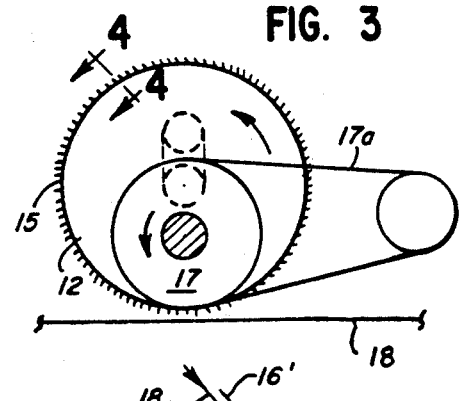
FIG. 3 is a sectional view taken along the sight line 3—3 applied to FIG. 2.

Still referring to FIG. 2, the numerals 11 and 12 designate a pair of wheels which are mounted on the frame in transversely spaced apart relation for rotation about angularly related axes as at 13 relative to the wheel 11 and 14 relative to the wheel 12. Additionally, the wheels along their peripheries are equipped with generally radially extending pins 15. The pins 15 are mounted in generally equally circumferentially spaced relation on each wheel 11 and 12—as can be appreciated from a consideration of FIG. 3.

Operation Generally

Referring again to FIG. 2, it will be seen that a patch 16 of elastic sheet material is installed on the pins 15 adjacent the upper ends of the wheels. As the wheels rotate about the axes 13 and 14 to the bottom position, the patch 16 is gradually stretched or lengthened to the configuration designated 16'.

The stretched patch 16' is thereupon removed from the pins by means of a removing mechanism 17 (see also FIG. 3) for application to one of the component webs 18. The web 18 has been previously equipped with longitudinally spaced apart bands or areas of adhesive by means of an adhesive applying unit designated 19 in the upper left hand portion of FIG. 1.

Figure 5:
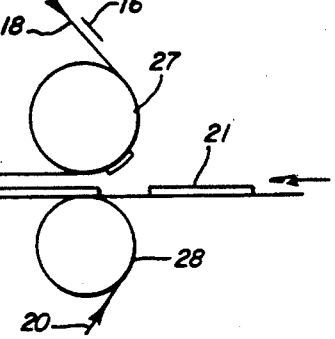
FIG. 5 is a fragmentary schematic side elevational view showing the application of the elastic-equipped non-woven web to the polyethylene web.

The diaper manufacturing operation is continued by combining the elastic-equipped non-woven web—see FIG. 5—and the polyethylene web 20, with the batts 21 disposed in spaced-apart relation between these two webs and between the elastic patches.

Apparatus

Referring now to FIG. 1, the frame 10 rotatably supports a cutoff roll 22—see the upper right hand corner. This cooperates with a vacuum anvil roll 23 to provide the patch of elastic sheet material 16 from a continuous web of such material designated 24. Here it will be appreciated that the continuous web of material 24 as well as the non-woven web 18 are provided from parent rolls (not shown). The patch 16 is held on the vacuum anvil roll 23 for a portion of the rotation of the roll 23 until it intersects the envelope of rotation of the pins 15 on the wheels 11 and 12. Here transfer occurs and a staking roll 23a presses the patch 16 into the pins 15 to assure that the patch does not fall off the pins. After the transfer occurs, the patch 16 is stretched while traveling on the rotating wheels 11 and 12.

As the patch 16 becomes aligned with the path of travel of the non-woven web 18, a further transfer occurs. For this purpose we provide the removing mechanism 17 consisting of a backup roll also designated 17 in the illustration given. This backup roll, like the rolls 22 and 23, is mounted for rotation within the frame 10—and between the two wheels 11 and 12. The backup roll 17 is driven by a belt and pulley system 17a (see FIG. 3).

Cooperating with the backup roll 17 is a bump roll 25 which has a raised portion 26. The portion 26 is synchronized with the appearance of a patch 16 and an adhesive area on the web 18 so that an adhesive application of the patch occurs at transfer to the non-woven web 18. During all of this, the web 18 is being advanced by pull rolls 27 and 28 also rotatably mounted within the frame 10. The rolls 27 and 28 are conventionally driven. Thus, the web 18 travels along a predetermined path within the side frames of the frame 10 which path continues to the left (as shown) after union is made with the spaced-apart batts and the polyethylene web.

It will be understood that the batts 21 are advanced to the nip between rolls 27 and 28 in spaced-apart relation by means of suitable conveyor belts as at 32 and 33. At the nip the batts 21 combine with the moisture impervious web 20. A chill roll 29 advances the web 20 to the nip and an adhesive applying unit 30 applies adhesive to the web 20 at the roll 29. This adhesive secures the foam to the web 20. A fine line glue assembly 31 applies glue to web 20 to secure the batts 21 and the web 20 together. As seen in FIG. 5, the now-combined webs 18, 20 are cut and severed to form a series of discrete diapers as at D.

Operation Specifically

Referring first to FIG. 1, the non-woven web 18 is advanced along a predetermined path P located between the side frames of the frame 10. Adhesive is applied at longitudinally spaced areas by means of the adhesive applicator 19.

Meanwhile, a continuous web of elastic sheet material 24 is advanced also from a parent roll (not shown) and toward a cutoff roll 22. The cutoff roll 22 cooperates with a vacuum anvil roll 23 to provide discrete segments of patches of foam material 16. These are then transferred to the pins 15 provided on the wheels 11 and 12 (see FIG. 2) and secured in place with staking roll 23a. The backup roll 17 is arranged to be positioned between the wheels 11 and 12 so as to apply the patch 16 onto the web 18 in the fashion indicated in the lower portion of FIG. 2.

In some instances, it may be advantageous to dispense with the vacuum anvil roll and cutoff roll and instead transversely perforate the web 24 upstream. In such a case, the web 24 is applied directly to the pins 15 on the wheels 11 and 12. The perforation bonds are broken at the time of transfer to web 18 under the influence of the rolls 17, 25. However, in such an instance, the wheels have to be operated at a surface speed slower than the speed of advance of the web 18 inasmuch as a 2" wide patch is applied only every 18" diaper length.

Figure 4:
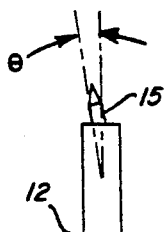
FIG. 4 is a sectional view taken along the sight line 4—4 applied to FIG. 3.

In the illustrated embodiment, however, the patches 16 travel at the same speed on the surface of the wheels 11, 12 as the web 18 and as the patch 16 reaches the position designated 16' in FIG. 2, the rolls 17 and 25 coact to press the patch 16' against the adhesive coated area of the web 18. This transfer can be facilitated by slightly inclining the pins 15 on the wheels 11, 12 as indicated at Θ in FIG. 4. In FIG. 4 the pins are slightly outwardly inclined and also may be slightly forwardly inclined, depending upon the character of the elastic material and the physical arrangement of the diaper machine.

Other means than pins may be advantageously employed such as vacuum, Velcro or belts for temporarily securing the patches 16 to the canted wheels.

It is also possible to phase the wheels 11, 12 by means of the drive 34—see the left hand portion of FIG. 2. By phasing, we refer to the fact that the axes 13, 14 are not only angularly related in the vertical plane (the angle a between a horizontal plane and the axis 13 or 14 in FIG. 2) but also in a horizontal plane (the angle between a vertical plane and the axis 13 or 14) so that different amounts of stretch can be provided with lesser or more angular travel of the patch 16 on the wheels 11, 12.

Returning to the illustrated embodiment, once the patch 16' has been applied to the web 18 as seen in FIG. 5, the combination passes around the pull roll 27 to combine the patch-equipped non-woven web 18 with the polyethylene web 20 and the batts 21. At this point in time, the polethylene web 20 has been equipped with adhesive not only to anchor the batts 21 but also to provide means for attaching the patch-equipped non-woven web 18.

While in the foregoing specification a detailed description of an embodiment of the invention has been set down for the purpose of illustration, many variations in the details herein given may be made by those skilled in the art without departing from the spirit and scope of the invention.

What is claimed is:

1. Apparatus for applying an elastic waistband in disposable diaper manufacture comprising:
    a frame defining a first longitudinally extending path for advancing a diaper component web;
    means operably associated with said frame for advancing said component web in said first path;
    means operably associated with said frame for applying adhesive to said web at longitudinally spaced portions
    said frame also defining a second longitudinally extending path intersecting said first path;
    a pair of spaced apart wheels mounted on said frame in said second path prior to the intersection of said paths for rotation about angularly related axes to pass through a first position and a second position spaced from said first position, said second position being at the intersection of said paths, said wheels each being equipped with a plurality of circumferentially spaced apart pins projecting generally radially outwardly from the wheel periphery;
    means on said frame in said second path for advancing elastic sheet material toward said wheels;
    means on said frame in said second path for transversely cutting said material to provide transversely elongated segments therefrom;
    means operably associated with said wheels for installing elastic sheet material on said pins at said first position;
    means operably associated with said frame for rotating said wheels to place said wheel peripheries closer together at said first position than at said second position whereby said elastic sheet material is stretched in moving from said first position to said second position;
    and pressure roll means on said frame between said wheels for sequentially disengaging said segments and substantially simultaneously pressing said segments against an adhesive-equipped portion of said web;
    said frame in said second path adjacent said first position being equipped with roll means for applying said segments to said pins, said roll means including a vacuum anvil roll positioned adjacent said pair of spaced apart wheels, a cutoff roll adjacent said vacuum roll and cooperative therewith to generate said segments, and a staking roll also adjacent said pair of spaced apart wheels but downstream in said path from said vacuum anvil roll.

* * * * *